(12) United States Patent
Hargett et al.

(10) Patent No.: US 9,868,606 B2
(45) Date of Patent: Jan. 16, 2018

(54) ROTARY DRUM APPARATUS RECONFIGURABLE FOR VARIOUS SIZE SUBSTRATES

(71) Applicant: The Procter & Gamble Company, Cincinnati, OH (US)

(72) Inventors: Mark Mason Hargett, Liberty Township, OH (US); Bradley Edward Walsh, Cincinnati, OH (US); David Carlton Ordway, Oxford, OH (US)

(73) Assignee: The Proctor & Gamble Company, Cincinnati, OH (US)

( * ) Notice: Subject to any disclaimer, the term of this patent is extended or adjusted under 35 U.S.C. 154(b) by 257 days.

(21) Appl. No.: 13/929,863

(22) Filed: Jun. 28, 2013

(65) Prior Publication Data

US 2014/0005019 A1   Jan. 2, 2014

Related U.S. Application Data

(60) Provisional application No. 61/665,938, filed on Jun. 29, 2012.

(51) Int. Cl.
  *B65H 5/00*   (2006.01)
  *B65H 27/00*  (2006.01)
  (Continued)

(52) U.S. Cl.
  CPC ....... *B65H 27/00* (2013.01); *A61F 13/15593* (2013.01); *A61F 13/15764* (2013.01);
  (Continued)

(58) Field of Classification Search
  CPC ........ F16C 13/00; F16C 13/022; B65H 27/00; B65H 3/0638; B65H 20/02; B65H 20/12;
  (Continued)

(56) References Cited

U.S. PATENT DOCUMENTS 3,674,194 A * 7/1972 Moesser ............... B65H 20/02
                                                     226/187
3,848,594 A   11/1974 Buell
(Continued)

FOREIGN PATENT DOCUMENTS

EP   0 565 606 B1   3/1995
EP   2 460 645 A1   6/2012
(Continued)

OTHER PUBLICATIONS

PCT/US2013/048583 PCT/International Search Report, dated Oct. 15, 2013.

(Continued)

*Primary Examiner* — Christopher Besler
(74) *Attorney, Agent, or Firm* — Sarah M. DeCristofaro; Abbey A. Lopez

(57) ABSTRACT

A rotary drum apparatus comprises a drum that is rotatable about an axis of rotation. The apparatus comprises a first set of first shell segments having a first number of first shell segments. Each first shell segment is releasably connectable with the drum and has an outer surface. The outer surfaces of the first shell segments combine to form a continuous first outer circumferential surface defining a maximum radial distance from the axis of rotation. The apparatus comprises a second set of second shell segments having a second number of second shell segments. Each second shell segment is releasably connectable with the drum and has an outer surface. The outer surfaces of the second shell segments combine to form a continuous second outer circumferential surface located within 10% of the maximum radial distance. The first number of first shell segments is greater than the second number of second shell segments.

14 Claims, 11 Drawing Sheets

(51) Int. Cl.

| | | |
|---|---|---|
| *F16C 13/00* | (2006.01) | |
| *B23C 3/00* | (2006.01) | |
| *B65H 20/12* | (2006.01) | |
| *A61F 13/15* | (2006.01) | |
| *B65H 29/24* | (2006.01) | |
| *B65H 35/08* | (2006.01) | |
| *B65H 39/14* | (2006.01) | |
| *B26D 1/40* | (2006.01) | |
| *B26D 5/00* | (2006.01) | |
| *B26D 7/20* | (2006.01) | |
| *B65H 5/12* | (2006.01) | |

(52) U.S. Cl.
CPC ............... *B23C 3/00* (2013.01); *B26D 1/405* (2013.01); *B26D 5/007* (2013.01); *B26D 7/204* (2013.01); *B65H 5/12* (2013.01); *B65H 20/12* (2013.01); *B65H 29/243* (2013.01); *B65H 35/08* (2013.01); *B65H 39/14* (2013.01); *F16C 13/00* (2013.01); *B65H 2404/114* (2013.01); *B65H 2406/33* (2013.01); *B65H 2601/324* (2013.01); *B65H 2801/57* (2013.01); *Y10T 29/49826* (2015.01)

(58) Field of Classification Search
CPC ...... B65H 2404/132; B65H 2404/1321; B65H 5/064; B65H 29/20; B65H 2404/112; B65H 2404/1121; B65H 2404/113; Y10T 29/49547; Y10T 29/49558
See application file for complete search history.

(56) References Cited

U.S. PATENT DOCUMENTS

| | | | |
|---|---|---|---|
| 3,860,003 A | 1/1975 | Buell | |
| 3,911,173 A | 10/1975 | Sprague, Jr. | |
| 3,929,135 A | 12/1975 | Thompson | |
| 4,324,246 A | 4/1982 | Mullane et al. | |
| 4,342,314 A | 8/1982 | Radel et al. | |
| 4,381,781 A | 5/1983 | Sciaraffa et al. | |
| 4,463,045 A | 7/1984 | Ahr et al. | |
| 4,573,986 A | 3/1986 | Minetola et al. | |
| 4,609,518 A | 9/1986 | Curro et al. | |
| 4,610,678 A | 9/1986 | Weisman et al. | |
| 4,629,643 A | 12/1986 | Curro et al. | |
| 4,662,875 A | 5/1987 | Hirotsu et al. | |
| 4,673,402 A | 6/1987 | Weisman et al. | |
| 4,695,278 A | 9/1987 | Lawson | |
| 4,785,996 A | 11/1988 | Ziecker et al. | |
| 4,795,454 A | 1/1989 | Dragoo | |
| 4,808,178 A | 2/1989 | Aziz et al. | |
| 4,834,735 A | 5/1989 | Alemany et al. | |
| 4,842,666 A | 6/1989 | Werenicz | |
| 4,846,815 A | 7/1989 | Scripps | |
| 4,857,067 A | 8/1989 | Wood et al. | |
| 4,888,231 A | 12/1989 | Angstadt | |
| 4,894,060 A | 1/1990 | Nestegard | |
| 4,909,803 A | 3/1990 | Aziz et al. | |
| 4,925,520 A | 5/1990 | Beaudoin et al. | |
| 4,946,527 A | 8/1990 | Battrell | |
| 4,963,140 A | 10/1990 | Robertson et al. | |
| 4,988,344 A | 1/1991 | Reising et al. | |
| 4,988,345 A | 1/1991 | Reising | |
| 5,006,394 A | 4/1991 | Baird | |
| 5,137,537 A | 8/1992 | Herron et al. | |
| 5,147,345 A | 9/1992 | Young et al. | |
| 5,151,092 A | 9/1992 | Buell et al. | |
| 5,221,274 A | 6/1993 | Buell et al. | |
| 5,260,345 A | 11/1993 | Desmarais et al. | |
| 5,342,338 A | 8/1994 | Roe | |
| 5,380,104 A * | 1/1995 | Garnett | B65G 39/09 384/480 |
| 5,387,207 A | 2/1995 | Dyer et al. | |
| 5,518,801 A | 5/1996 | Chappell et al. | |
| 5,562,646 A | 10/1996 | Goldman et al. | |
| 5,571,096 A | 11/1996 | Dobrin et al. | |
| 5,580,411 A | 12/1996 | Nease et al. | |
| 5,595,567 A | 1/1997 | King et al. | |
| 5,624,427 A | 4/1997 | Bergman et al. | |
| 5,650,222 A | 7/1997 | Desmarais et al. | |
| 5,669,894 A | 9/1997 | Goldman et al. | |
| 5,674,216 A | 10/1997 | Buell et al. | |
| 5,691,035 A | 11/1997 | Chappell et al. | |
| 5,693,165 A | 12/1997 | Schmitz | |
| 5,723,087 A | 3/1998 | Chappell et al. | |
| 5,735,840 A | 4/1998 | Kline et al. | |
| 5,836,500 A * | 11/1998 | Jourde | 226/189 |
| 5,865,823 A | 2/1999 | Curro | |
| 5,916,663 A | 6/1999 | Chappell et al. | |
| 5,928,212 A | 7/1999 | Kline et al. | |
| 5,941,864 A | 8/1999 | Roe | |
| 6,004,306 A | 12/1999 | Roe et al. | |
| 6,010,491 A | 1/2000 | Roe et al. | |
| 6,027,483 A | 2/2000 | Chappell et al. | |
| 6,251,097 B1 | 6/2001 | Kline et al. | |
| 6,414,215 B1 | 7/2002 | Roe | |
| 6,432,098 B1 | 8/2002 | Kline et al. | |
| 6,441,266 B1 | 8/2002 | Dyer et al. | |
| 6,494,244 B2 | 12/2002 | Parrish et al. | |
| 6,573,423 B1 | 6/2003 | Herrlein et al. | |
| 6,596,108 B2 | 7/2003 | McCabe | |
| 6,677,258 B2 | 1/2004 | Carroll et al. | |
| 6,739,489 B1 * | 5/2004 | Nicolai et al. | 226/95 |
| 7,811,403 B2 | 10/2010 | Andrews | |
| 8,377,249 B2 | 2/2013 | Gill | |
| 2004/0162536 A1 | 8/2004 | Becker et al. | |
| 2004/0167486 A1 | 8/2004 | Busam et al. | |
| 2005/0215972 A1 | 9/2005 | Roe et al. | |
| 2005/0215973 A1 | 9/2005 | Roe et al. | |
| 2006/0189956 A1 | 8/2006 | Vatansever | |
| 2007/0078427 A1 | 4/2007 | Raycheck et al. | |
| 2007/0093769 A1 | 4/2007 | Kline et al. | |
| 2007/0142798 A1 | 6/2007 | Goodlander et al. | |
| 2007/0142806 A1 | 6/2007 | Roe et al. | |
| 2007/0219521 A1 | 9/2007 | Hird et al. | |
| 2007/0287348 A1 | 12/2007 | Autran et al. | |
| 2007/0287982 A1 | 12/2007 | Lodge et al. | |
| 2007/0287983 A1 | 12/2007 | Autran et al. | |
| 2009/0294044 A1 | 12/2009 | Gill | |
| 2010/0252603 A1 | 10/2010 | Gill | |
| 2011/0139657 A1 | 6/2011 | Hird et al. | |
| 2011/0139658 A1 | 6/2011 | Hird et al. | |
| 2011/0139659 A1 | 6/2011 | Hird et al. | |
| 2011/0139662 A1 | 6/2011 | Hird et al. | |
| 2011/0152812 A1 | 6/2011 | Hird et al. | |

FOREIGN PATENT DOCUMENTS

| | | |
|---|---|---|
| EP | 2 554 145 A1 | 2/2013 |
| WO | WO 1995/16746 | 6/1995 |
| WO | WO 2000/002727 A1 | 1/2000 |
| WO | WO 2005/035414 A1 | 4/2005 |
| WO | WO 2006/015141 | 2/2006 |
| WO | WO 2009/083791 A1 | 7/2009 |
| WO | WO 2009/146307 A1 | 12/2009 |

OTHER PUBLICATIONS

U.S. Appl. No. 13/929,854, filed Jun. 28, 2013, Mark Mason Hargett.

* cited by examiner

ROTARY DRUM APPARATUS RECONFIGURABLE FOR VARIOUS SIZE SUBSTRATES

FIELD OF THE INVENTION

The present disclosure relates generally to rotary drum apparatuses, and more particularly, relates to rotary drum apparatuses that are reconfigurable for advancing discrete lengths of elastic substrate of various sizes.

BACKGROUND OF THE INVENTION

Along an assembly line, various types of articles, such as diapers and other absorbent articles, may be assembled by adding components to and otherwise modifying an advancing, continuous web of material. In some processes, advancing webs of material are combined with other advancing webs of material. In other processes, individual components created from advancing webs of material are combined with advancing webs of material, which in turn, are then combined with other advancing webs of material. Webs of material and component parts used to manufacture diapers may include: backsheets, topsheet, absorbent cores, front and/or back ears, fastener components, and various types of elastic webs and components such as leg elastics, barrier leg cuff elastics, and waist elastics. Once the desired component parts are assembled, the advancing web or webs and component parts are subjected to a final cut to separate the web or webs into discrete diapers or other absorbent articles. The discrete diapers or absorbent articles may also then be folded and packaged.

Some processes are configured to advance substrates on a rotating drum, and, in particular, to advance elastic substrates in a stretched state on the drum. The elastic substrate may be cut into discrete lengths of elastic substrate while advancing on the drum. Sometimes, the drum may include anvils for cutting the substrate while advancing on the drum. In some processes, the drum may include a vacuum system to hold the discrete lengths of elastic substrate in a stretched state on the drum. The drum may be configured for processing a particular size discrete length of elastic substrate. For example, anvils may be spaced circumferentially at predetermined distances around the drum for cutting the substrate into discrete lengths of elastic substrate of a predetermined size. In addition, the drum may include vacuum apertures configured to maintain stretch in a discrete length of elastic substrate of a predetermined size. Such drums may not be adaptable to or reconfigurable to accept more than one size discrete length of elastic substrate. As such, it may be necessary to change drums on an assembly line in order to process discrete lengths of elastic substrate of different sizes. For example, the size of a drum may increase as the size of the discrete lengths of elastic substrate increase. In turn, as the size of the drum increases, the mass may increase and so may the cost to manufacture the drum or drums. Additionally, a production line configured for one size drum may have to be reconfigured in order to operate in conjunction with a different size drum, which may include moving or replacing equipment. The process of replacing drums and reconfiguring the production line can be time consuming and labor intensive. Due to the size and mass of the drum, additional labor and/or mechanical assistance may be required to change the drums.

It may be desirable to provide a drum capable of processing discrete lengths of elastic substrate of various sizes, while maintaining the overall dimensions of the drum.

SUMMARY OF THE INVENTION

Aspects of the present disclosure involve rotary drum apparatuses that are reconfigurable for advancing and cutting substrates into discrete lengths of elastic substrate of various sizes. In one form, an apparatus comprises a drum rotatable about an axis of rotation. The rotary drum apparatus comprises a first set of first shell segments having a first number of first shell segments. Each first shell segment is releasably connectable with the drum, and each first shell segment has an outer surface. When the first number of the first shell segments are connected with the drum, the outer surfaces combine to form a continuous first outer circumferential surface defining a maximum radial distance from the axis of rotation. The rotary drum apparatus comprises a second set of second shell segments having a second number of shell segments, each second shell segment being releasably connectable with the drum, and each second shell segment having an outer surface. When the second number of the second shell segments are connected with the drum, the outer surfaces combine to form a continuous second outer circumferential surface located within 10% of the maximum radial distance. The first number of first shell segments is greater than the second number of second shell segments.

In another form, an apparatus comprises a shell member having a curved outer surface. The shell member defines a first end and a second end. The outer surface of the shell member comprises a plurality of vacuum apertures. The apparatus comprises a first support member that is releasably connectable with the first end of the shell member and a second support member that is releasably connectable with the second end of the shell member. The apparatus comprises an anvil releasably that is connectable with each of the first and second support members and located adjacent to the outer surface of the shell member. The apparatus comprises a grip plate that is connected with the outer surface of the shell member and located relatively near each of the first and second ends of the shell member. The grip plates define an outer edge, the outer edge of the grip plates having a rough surface. The apparatus comprises a vacuum member that is releasably connectable with the shell member. The vacuum apertures are in fluid communication with the vacuum member.

In another form, a method for configuring a rotary drum apparatus for advancing a discrete length of elastic substrate of substrate of a particular size comprises the steps of: providing a drum rotatable about an axis of rotation, the drum comprising a first set of first shell segments having a first number of first shell segments, each first shell segment releasably connectable with the drum, and each first shell segment having an outer surface, and when the first number of the first shell segments are connected with the drum, the outer surfaces combine to form a continuous first outer circumferential surface defining a maximum radial distance from the axis of rotation; removing the first set of shell segments from the drum; providing a second set of second shell segments having a second number of shell segments, each second shell segment releasably connectable with the drum, and each second shell segment having an outer surface, and when the second number of the second shell segments are connected with the drum, the outer surfaces combine to form a continuous second outer circumferential surface located within 10% of the maximum radial distance from the axis of rotation, wherein the first number of first shell segments is greater than the second number of second shell segments; and connecting the second set of second shell segments with the drum.

DETAILED DESCRIPTION OF THE INVENTION

Figure 1:
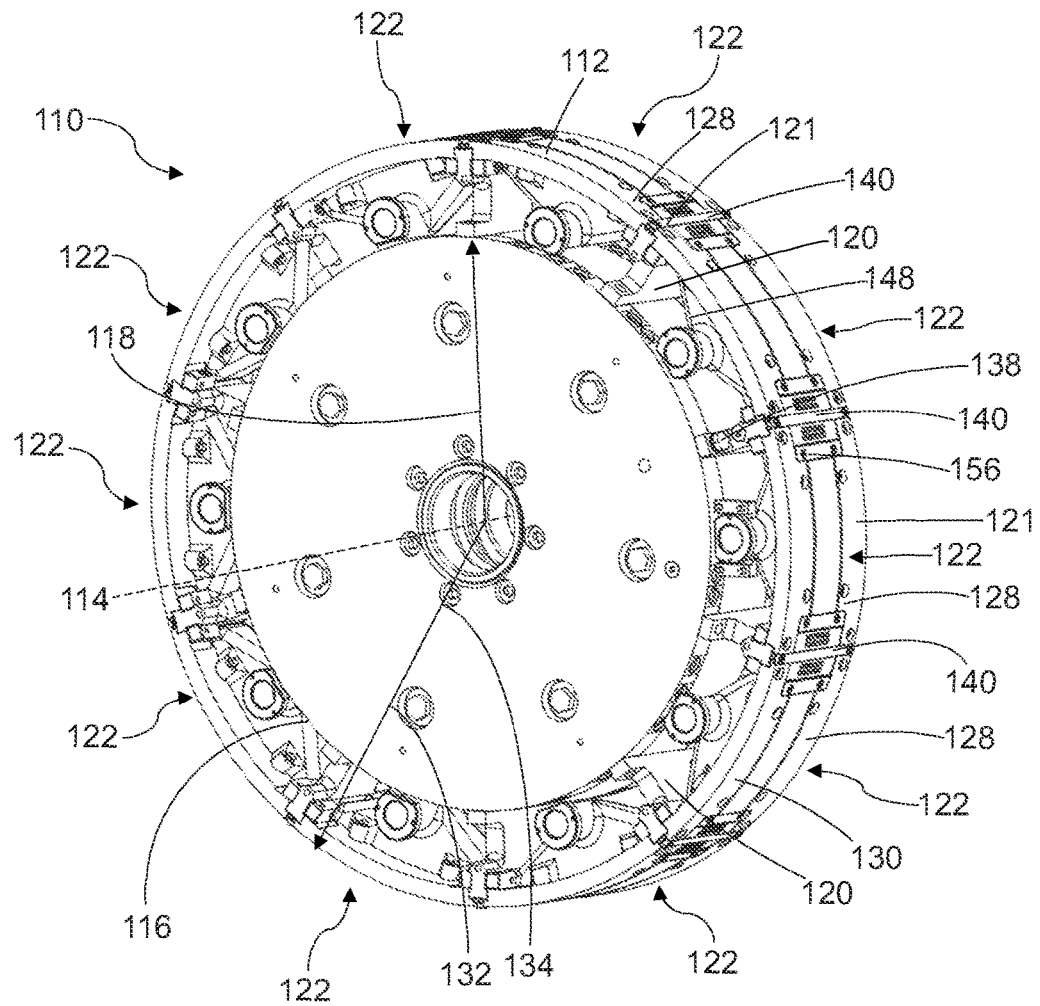
FIG. 1 is a schematic perspective, side view of a rotary drum apparatus.

This application claims priority to U.S. Provisional Application Ser. No. 61/665,938, filed Jun. 29, 2012, which is hereby incorporated by reference in its entirety.

The following definitions may be useful in understanding the present disclosure:

"Absorbent article" is used herein to refer to consumer products whose primary function is to absorb and retain soils and wastes.

"Diaper" is used herein to refer to an absorbent article generally worn by infants and incontinent persons about the lower torso.

"Disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

"Disposed" is used herein to mean that an element(s) is formed (joined and positioned) in a particular place or position as a macro-unitary structure with other elements or as a separate element joined to another element.

"Joined" is used herein to encompass configurations whereby an element is directly secured to another element by affixing the element directly to the other element, and configurations whereby an element is indirectly secured to another element by affixing the element to intermediate member(s) which in turn are affixed to the other element.

"Radial" means a direction running from an axis of rotation of a drum toward an outer circumferential surface of the drum.

"Substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a layer or layers or fibrous materials, films and foils such as plastic films or metallic foils that may be used alone or laminated to one or more web, layer, film and/or foil. As such, a web is a substrate.

"Nonwoven" refers herein to a material made from continuous (long) filaments (fibers) and/or discontinuous (short) filaments (fibers) by processes such as spunbonding, meltblowing, and the like. Nonwovens do not have a woven or knitted filament pattern.

An "elastic," "elastomer" or "elastomeric" refers to any material that upon application of a force to its relaxed, initial length can stretch or elongate to an elongated length more than 10% greater than its initial length and will substantially recover back to about its initial length upon release of the applied force. The term "inelastic" refers herein to any material that does not fall within the definition of "elastic".

"Activation" is the mechanical deformation of an extensible material that results in permanent elongation of the extensible material in the direction of activation in the X-Y plane of the material. For example, activation occurs when a web or portion of a web is subjected to a stress that causes the material to strain beyond the onset of plasticity, which may or may not include complete mechanical failure of the material or portion of the material. Activation of a layered elastic substrate that includes an elastic material joined to an extensible material typically results in the extensible material deforming plastically, while the elastic material returns substantially to its original dimension. "Activated" means a material that has been subjected to an activation process.

"Machine direction" (MD) is used herein to refer to the direction travel of a substrate through a process.

"Cross direction" (CD) is used herein to refer to a direction that is generally not parallel to, and usually perpendicular to, the machine direction in the XY plane of the material.

Aspects of the present disclosure involve apparatuses and methods utilizing continuous lengths of substrate for manufacturing absorbent articles, and more particularly, apparatuses for advancing continuous lengths of elastic substrate in a stretched state. As discussed below, such methods and apparatuses may include a rotary drum that may be configured for cutting an elastic substrate into discrete lengths of elastic substrate of a predetermined size while advancing the discrete length of elastic substrate on the drum. The rotary drum apparatus may be configured to apply vacuum to hold the discrete lengths of elastic substrate in a stretched state on the drum. The rotary drum apparatus may be reconfigured for cutting and maintaining stretch in advancing discrete lengths of elastic substrate of various sizes. More specifically, the apparatuses and methods may be useful for providing a rotary drum apparatus that is reconfigurable for handling discrete lengths of elastic substrate of various sizes while retaining the overall dimensions of the drum.

In general, a rotary drum apparatus may comprise a drum rotatable about an axis of rotation. The drum is defined by an inner circumferential surface located at an inner radial distance from the axis of rotation. The rotary drum apparatus may comprise a set of shell segments releasably connectable with the inner circumferential surface of the drum. The shell segments may be defined by an outer surface. The outer surface of the shell segments may be curved. The shell segments are configured to connect with the inner circumferential surface of the drum to form a continuous outer circumferential surface around the inner circumferential surface of the drum. The outer circumferential surface may be located at an outer radial distance from the axis of rotation. The outer radial distance defines a maximum radial distance from the axis of rotation. The rotary drum apparatus may include one or more sets of shell segments capable of forming the outer circumferential surface of the drum. Each set of shell segments may be releasably connectable with the drum to form an outer circumferential surface of the drum located within 10% of the maximum radial distance. Each set of shell segments may be configured for discrete lengths of elastic substrate of a predetermined size. Maintaining the overall dimensions of the drum with each set of shell segments allows for the simplified transformation of a production line for handling discrete lengths of elastic substrate of different sizes.

As discussed in more detail below, the shell segment includes a support member releasably connectable with the inner circumferential surface of the drum and a shell member releasably connectable with the support member. The shell members may be configured with vacuum apertures for applying vacuum pressure to hold the discrete lengths of elastic substrate in a stretched state on the outer circumferential surface of the drum. The vacuum apertures may be in fluid communication with a vacuum member that is located radially inward from the outer circumferential surface of the drum and releasably connectable with the shell member. The rotary drum apparatus may also include an anvil that is releasably connectable with the support member and located between adjacent shell members in the outer circumferential surface of the drum.

It is to be appreciated that although the methods and apparatuses herein may be configured to advance and cut various sizes of discrete lengths of elastic substrate, the methods and apparatuses are discussed below in the context of manufacturing absorbent articles. In particular, the methods and apparatuses are discussed in the context of advancing and cutting continuous lengths of elastic substrate into discrete lengths of elastic substrate in the form of elastic waistbands. While the present disclosure relates mainly to advancing discrete lengths of elastic substrate such as waistbands to be joined with absorbent articles, it is to be appreciated that the methods and apparatuses disclosed herein can also be used for advancing and cutting other components used on diapers as well as other types of absorbent articles. For example, elastic components can include pre-stretched ears or side panels, leg cuffs, and elasticized topsheets. While the methods and apparatuses herein are discussed in the context of discrete lengths of elastic substrate, it is to be appreciated that the present invention may be used to advance and cut inelastic substrates into discrete components of various sizes. Inelastic components may include backsheets, topsheet, absorbent cores, front and/or back ears, and fastener components.

In one exemplary configuration, FIG. 1 shows a rotary drum apparatus 110 including a drum 112 rotatable about an axis of rotation 114. The drum 112 comprises an inner circumferential surface 116 located at an inner radial distance $R_I$ from the axis of rotation 114. The rotary drum apparatus 110 may include shell segments 122 that are releasably connectable with the inner circumferential surface 116 of the drum 112. The shell segments 122 connect with the inner circumferential surface 116 of the drum 112 to form a continuous outer circumferential surface 130 around the drum 112 located at an outer radial distance $R_O$ from the axis of rotation 114. It is to be appreciated that the continuous outer circumferential surface 130 may include gaps between adjacent shell segments 122. The outer circumferential surface 130 may define a maximum radial distance $R_M$ from the axis of rotation 114. As shown in FIG. 1, the outer radial distance $R_O$ is greater than the inner radial distance $R_I$. The rotary drum apparatus 110 may comprise more than one set of shell segments 122, each set of shell segments 122 may be releasably connectable with the inner circumferential surface 116 of the drum 112 and capable of forming the outer circumferential surface 130 around the drum 112 at an outer radial distance $R_O$ from the axis of rotation 114. It is to be appreciated that for each set of shell segments 122, the outer radial distance $R_O$ may be located at the maximum radial distance $R_M$ or within 10% of the maximum radial distance $R_M$ from the axis of rotation 114 in order to maintain the overall dimensions of the drum 112.

With continuing reference to FIG. 1, each shell segment 122 may include a support member 120 that is releasably connectable with the inner circumferential surface 116 of the drum 112 and a shell member 121 that is releasably connectable with the support member 120. While the support member 120 shown in FIG. 1 is connected with the first outer surface 116 with a bolt 138, it is to be appreciated that the support members 120 may be connected with the inner circumferential surface 116 of the drum 112 in various ways, such as, for example, bolts, screws, pins, or keys and matching key ways. Each shell segment 122 may also include an anvil 140 releasably connectable with the support member 120 of the shells segment 122. The anvils 140 and the shell members 121 connect with the support members 120 to form the outer circumferential surface 130 around the drum 112. As shown in FIG. 1, the anvils 140 are located between adjacent shell members 121. It is to be appreciated that the shell segment may comprise various materials. For example, the support members 120 may be made of steel and the shell members 121 may be made of aluminum.

Figure 2A:
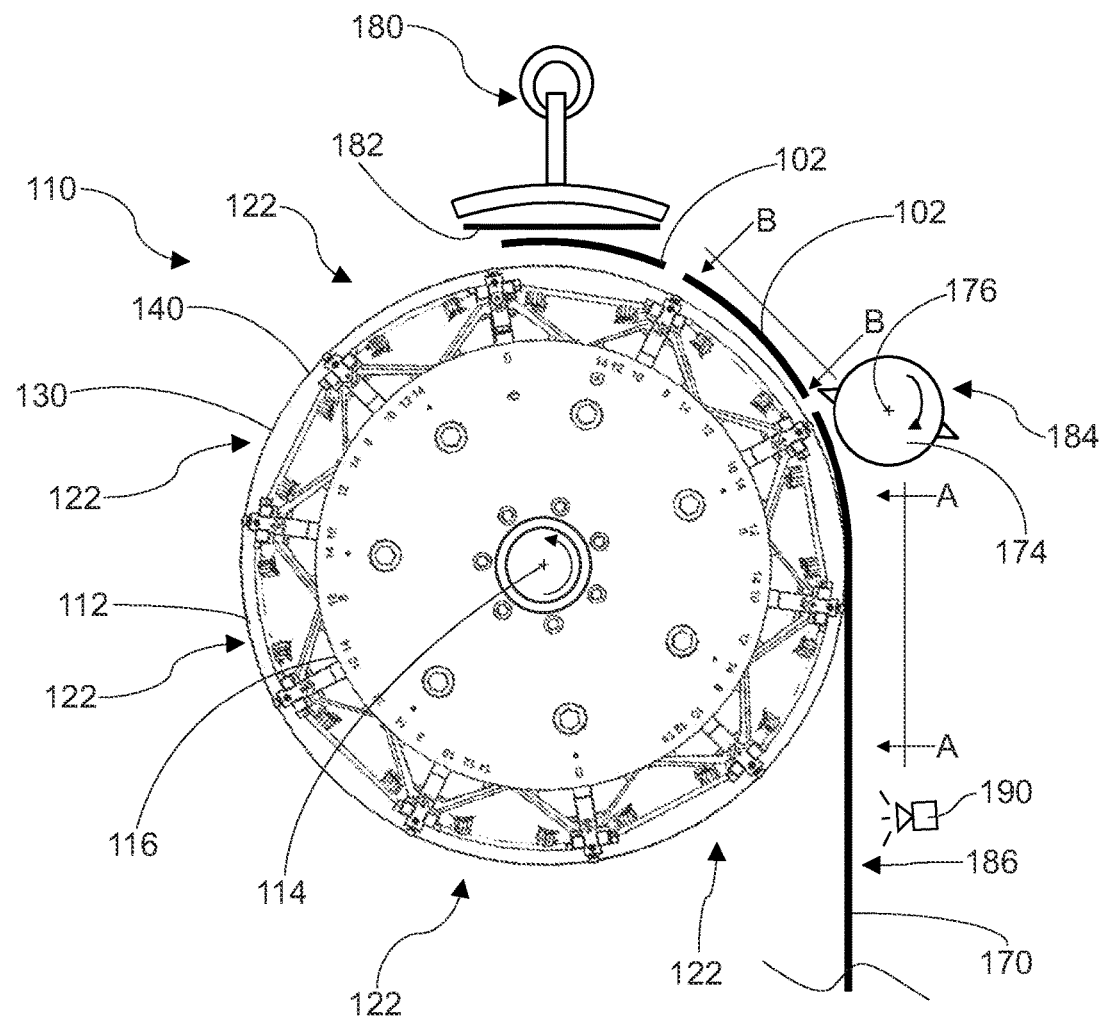
FIG. 2A is a schematic, side elevation view of a rotary drum apparatus and a cutter positioned adjacent to the rotary drum.
Figure 2B:
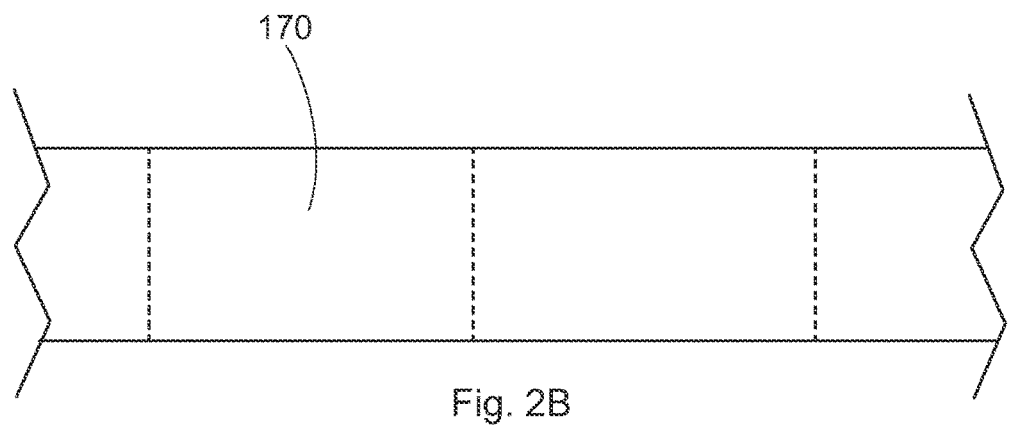
FIG. 2B is a schematic, plan view of a continuous length of elastic substrate from FIG. 2A taken along line A-A.
Figure 2C:
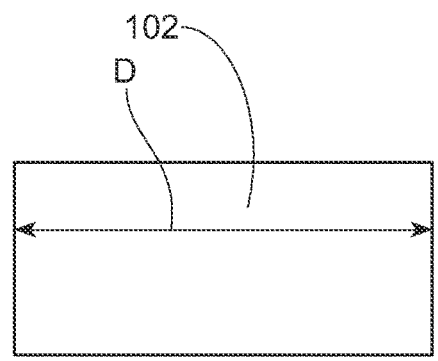
FIG. 2C is a schematic, plan view of a discrete length of elastic substrate from FIG. 2A taken along line B-B.

FIG. 2A shows a rotary drum apparatus 110 and a cutter 184, shown in the form of a cutting roll 174 for purposes of illustration, located adjacent to the rotary drum apparatus 110. The rotary drum apparatus 110 includes a drum 112 having an inner circumferential surface 116 and a set of shell segments 122 attached thereto. The shell segments 122 combine to form the outer circumferential surface 130 around the inner circumferential surface 116 of the drum 112. The shell segments 122 include shell members 121 separated by anvils 140 in the outer circumferential surface 130 of the drum 112. The cutting roll 174 rotates about an axis of rotation 176. In operation, a continuous length of elastic substrate 170 is advanced in a machine direction MD onto the outer circumferential surface 130 of the drum 112 in a stretched state, as shown in FIGS. 2A and 2B. While advancing on the outer circumferential surface 130 of the drum 112, the elastic substrate 170 is cut by the rotating cutting roll 174 into discrete lengths of elastic substrate 102, shown in FIG. 2C in the form of waistbands 294 for purposes of illustration, having a predetermined length D. As discussed in more detail below, the shell members 121 are configured with vacuum apertures to apply vacuum to maintain the discrete lengths of elastic substrate 102 in a stretched state on the outer circumferential surface 130 of the drum 112.

Figure 2D:
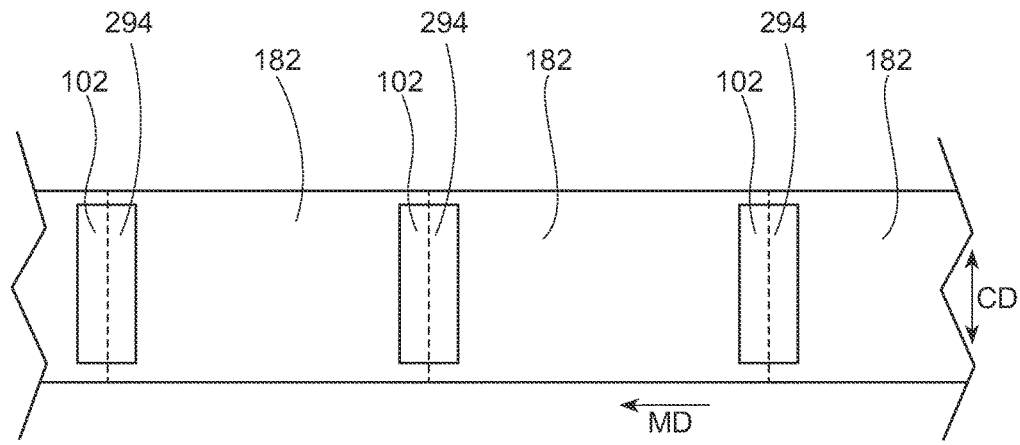
FIG. 2D is a schematic, plan view of a continuous length of absorbent articles having elastic waistbands.
Figure 2E:
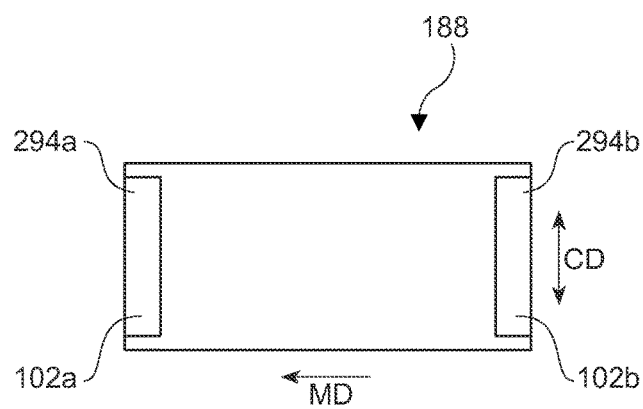
FIG. 2E is a schematic, plan view of an individual absorbent article having two elastic waistbands.

It is to be appreciated that the discrete lengths of elastic substrate may be transferred from the drum to other processing stations. For example, as shown in FIGS. 1 and 2A, the discrete lengths of elastic substrate 102 advancing on the drum 112 may be joined with a continuous length of absorbent articles 182 advancing in a cross direction CD relative to the machine direction MD of the advancing discrete lengths of elastic substrate 102. A tamper apparatus 180 located adjacent the drum 112 may direct a portion of the continuous length of absorbent articles 182 toward the discrete length of elastic substrate 102 on the drum. Adhesive 186 may be applied to the continuous length of elastic substrate 170 by an adhesive applicator 190 to bond the discrete length of elastic substrate 102 to the continuous length of absorbent articles 182. Vacuum may be intermittently interrupted to assist the discrete lengths of elastic substrate 102 in releasing from the outer circumferential surface 130 of the drum 112. The discrete lengths of elastic substrate 102 may be joined to the continuous length of absorbent articles 182 in a stretched state, spaced apart from each other discrete length of elastic substrate in the machine direction MD relative to the advancing continuous length of absorbent articles 182 as shown in FIG. 2D. As shown in FIGS. 2D and 2E, the continuous length of absorbent articles 182 may be cut into individual absorbent articles 188 by cutting the absorbent articles 182 in the cross direction CD relative to the machine direction MD of the advancing absorbent articles 182 to create absorbent articles 188 having two discrete lengths of elastic substrate 102a and 102b, shown in the form of elastic waistbands 294a and 294b for purposes of illustration.

The rotary drum apparatus 110 may be used with various methods and apparatuses for joining discrete lengths of elastic substrate to an advancing substrate such as those described in U.S. Provisional Patent No. 61/665,930; U.S. Provisional Patent Application No. 61/665,928; U.S. Provisional Patent Application No. 61/665,933; U.S. Provisional Application No. 61/666,087; U.S. Pat. No. 5,693,165; U.S. Pat. No. 6,596,108; U.S. Pat. No. 6,494,244; U.S. Pat. No. 7,811,403; and U.S. Publication Nos. 2010/0252603 and 2009/0294044, for example.

Figure 3:
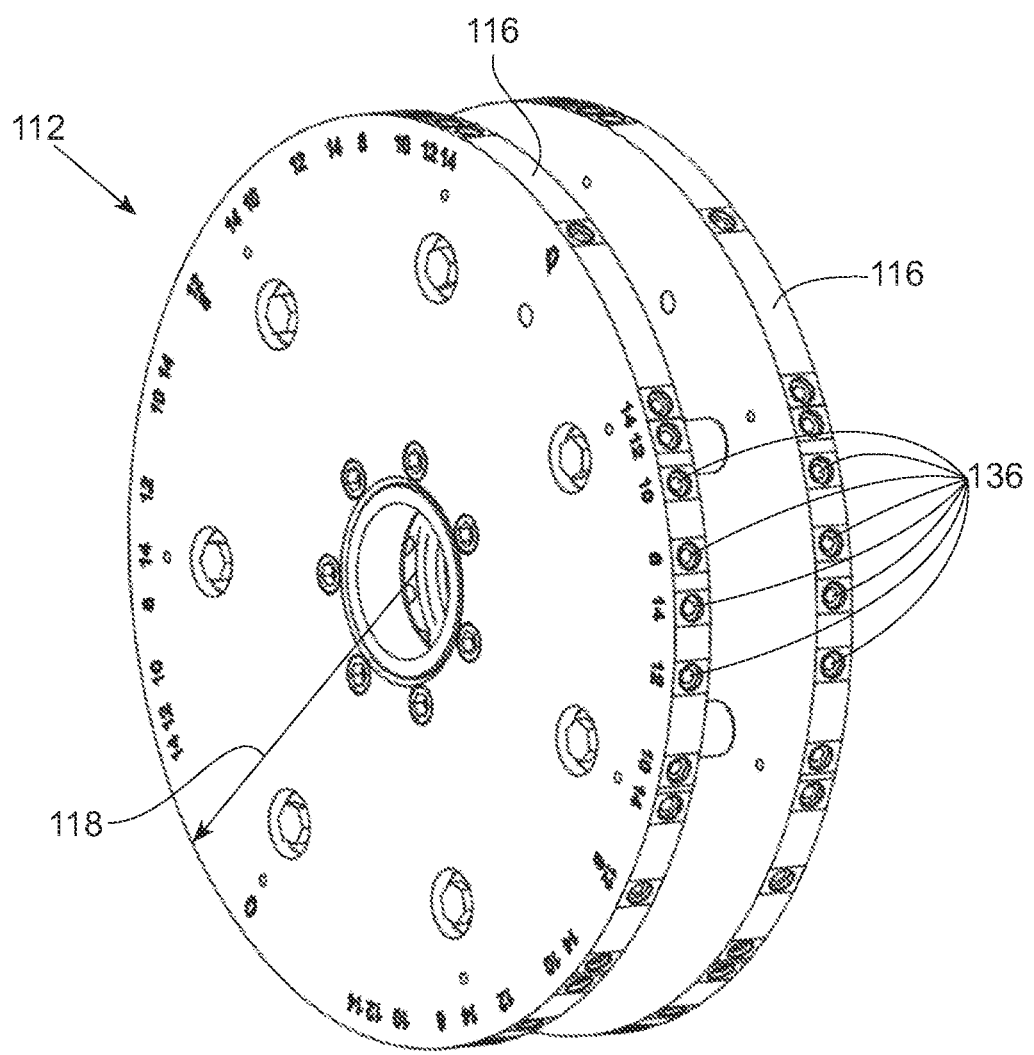
FIG. 3 is a perspective, side view of a drum.

FIG. 3 shows a portion of a drum 112 having multiple connection sites 136 spaced circumferentially around the inner circumferential 116 surface of the drum 112. With reference to FIGS. 1 and 3, it is to be appreciated that the support members 120 are connectable with the various connection sites 136 on the inner circumferential surface 116 of the drum 112. The support members 120 of one set of shell segments may be used for different sets of shell segments 122 such that the support members 120 are connectable with shell members 121 of different sizes. It is to be appreciated that the drum 112 may be fabricated from various materials. For example, the drum 112 may be made of steel.

Figure 4:
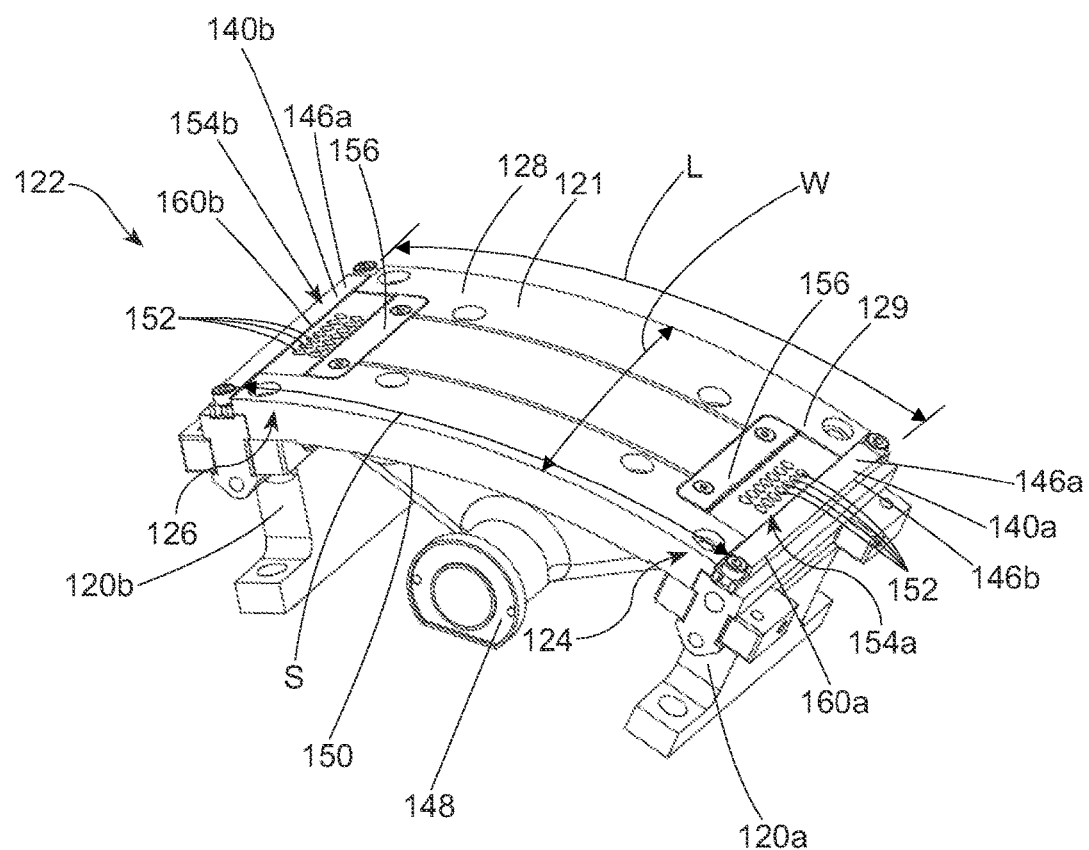
FIG. 4 is a perspective, side view of a shell segment.

FIG. 4 shows a shell member 121 that is releasably connectable with the support member 120a and the support member 120b of an adjacent shell segment. Each shell segment 122 may also include an anvil 140a releasably connectable with the support member 120a. A shell segment 122 may be defined by an outer surface 128 having a circumferential length L that extends from a first edge 160a of the anvil 140a to a first edge 160b of an anvil 140b of an adjacent shell segment. The shell segment 122 may also be defined by a width W. The width W may also define the width of the outer circumferential surface 130 of the drum 112. The shell member 121 defines by an outer surface 129 having a circumferential length S. As shown in FIG. 4, the outer surface 129 of a shell member 121, and thus the outer surface 128 of the shell segment 122, may be curved. However, it is to be appreciated that the outer surface 129 of the shell member 121, and thus the outer surface 128 of the shell segment 122, may be substantially flat. The shell member 121 may connect with the support member 120 in various ways. For example, the shell member 121 may connect with the support member 120 using bolts, screws, pins, tab and slot connections, or keys and matching keyways.

Figure 5:
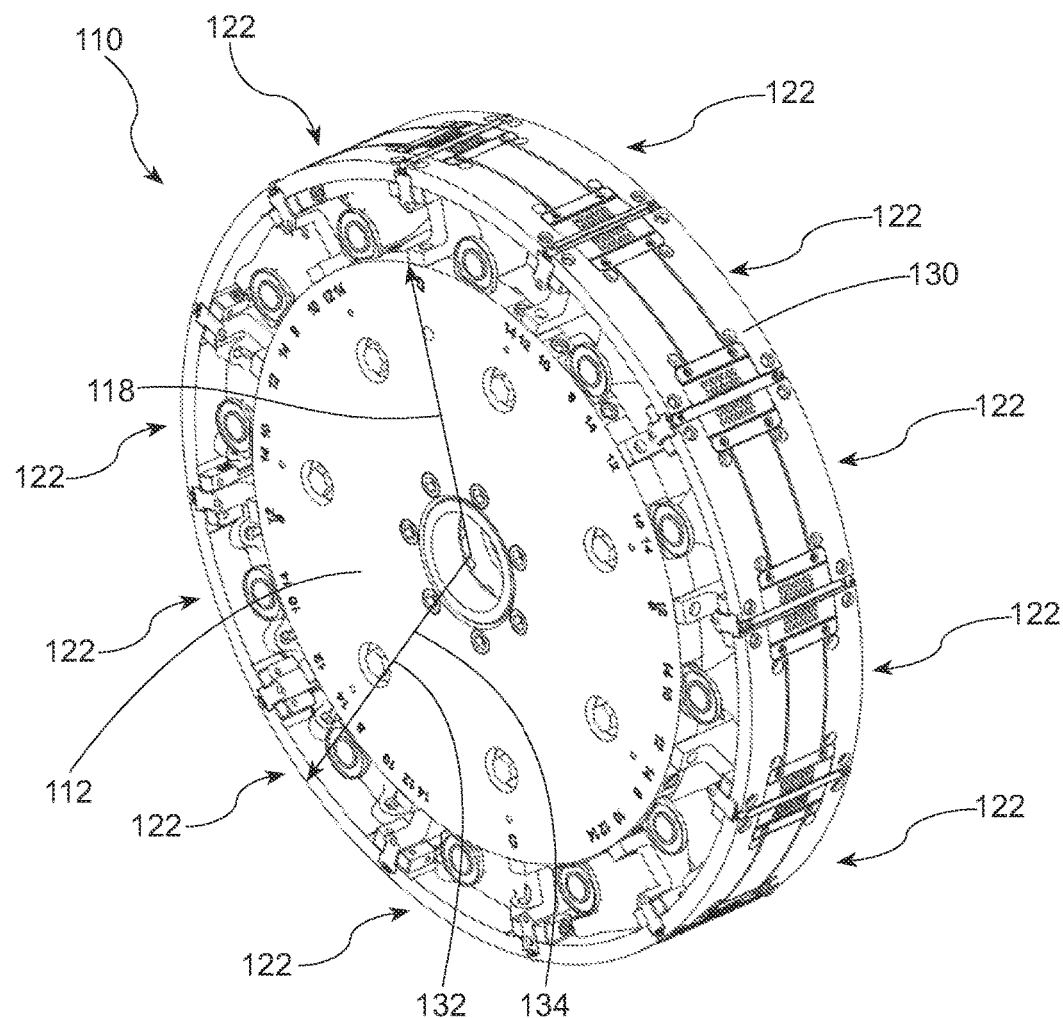
FIG. 5 is a perspective, side view of a rotary drum apparatus.

With continuing reference to FIG. 4, each shell segment 122 in a set may have the same circumferential length L and width W. In such an exemplary configuration, the support members 120 of the shell segment 122 may be spaced at equal circumferential lengths from each other support member 120 on the inner circumferential surface 116 of the drum 112 as shown in FIG. 5. However, it is to be appreciated that a set of shell segments 122 may include shell segments 122 having different circumferential lengths L and widths W. As such, the support members 120 of the shell segments 122 may be spaced at different circumferential lengths from each adjacent support member 120 around the inner circumferential surface 116 of the drum 112.

With reference back to FIGS. 1, 2A, and 2C, a set of shell segments 122 may be configured to advance a discrete length of elastic substrate 102 of a predetermined length D. It is to be appreciated that the longer the predetermined length D of the discrete length of elastic substrate 102, the greater the circumferential length L of the shell segment. As a result, the longer the predetermined length D of the discrete length of elastic substrate 102, the fewer number of shell segments 122 in the set and the further apart the support members 120 of the shell segments 122 are spaced circumferentially around the inner circumferential surface 116 of the drum 112. Conversely, the shorter the predetermined length D of the discrete length of elastic substrate 102, the shorter the circumferential length L of the shell segment 122, and greater number of shell segments 122 in the set. In addition, the shorter the predetermined length D of the discrete length of elastic substrate 102, the closer the support members 120 of the shell segment 122 are spaced circumferentially around the inner circumferential surface 116 of the drum 112. It is to be appreciated that if each set of shell segments 122 of the rotary drum apparatus 110 combines to form the outer circumferential surface 130 at the maximum radial distance $R_M$ from the axis of rotation 114, than the circumferential length L of the shell segments 122 in a set directly correlates with the number of shell segments 122 in the set.

As shown in FIG. 1, a rotary drum apparatus 110 may include a set of shell segments 122 having ten shell segments 122. In some exemplary configurations, such as shown in FIG. 5, a rotary drum apparatus 110 may include a set of twelve shell segments 122. In some exemplary configurations, each set of shell segments may include a different number of shell segments. For example, a set of shell segments may include 4, 5, 6, 7, 8, 9, 10, 11, 12, 13, 14, 15, 16 or various other numbers of shell segments.

With reference to FIGS. 1 and 4, in some exemplary configurations, the outer circumferential surface 130 may be located at the maximum radial distance $R_M$ for each set of shell segments 122 of the rotary drum apparatus 110. As such, when each set of shell segments 122 connects with the inner circumferential surface 116 of the drum, the shell segments 122 in the set combine to form the outer circumferential surface 130 located at the maximum radial distance $R_M$. As discussed above, maintaining the overall dimension of the drum 112 with each set of shell segments 122 reduces the time and labor required to reconfigure various other equipment in the production line. While each set of shell segments 122 may combine to form an outer circumferential surface 130 at the maximum radial distance $R_M$ from the axis of rotation 114, in some exemplary configurations, a set of shell segments 122 may combine to form an outer circumferential surface 130 that is located at an outer radial distance $R_O$ that is within 10% of the maximum radial distance $R_M$. In other exemplary configurations, a set of shell segments 122 may combine to form a outer circumferential surface 130 located at an outer radial distance $R_O$ that is within 1%, 2%, 3%, 4%, 5%, 6%, 7%, 8%, 9%, or 10% of the maximum radial distance $R_M$. As such, in some exemplary configurations, the outer circumferential surface 130 of the drum 112 may be located at an outer radial distance $R_O$ that is different from the maximum radial distance $R_M$, which may result in only minimal adjustments to adjacent equipment in the process for handling discrete lengths of elastic substrate of different sizes. In addition, in some exemplary configurations, each set of shell segments 122 may have a constant width W. However, it is to be appreciated that each set of shell segments may have different widths.

As discussed above, with continuing reference to FIGS. 1 and 4, the shell segments 122 may include an anvil 140 releasably connectable with each support member 120 and located adjacent the individual shell members 121. The anvil 140 may be defined by outer surfaces 146a and 146b. Outer surface 146a of the anvil 140 may form a part of the first outer circumferential surface 130 of the drum 112 while an opposing outer surface (not shown) may connect with the support member 120. As discussed above, and as shown in FIGS. 4 and 5, the outer surface 146a of the anvils 140 and the outer surface 129 of the shell members 121 combine to form the outer circumferential surface 130 of the drum 112. The anvil 140 may be rotated and connected with the support member 120 such that outer surface 146a contacts the support member 120 and an opposite outer surface (not shown) forms a part of the outer circumferential surface 130 of the drum 112. It is to be appreciated that the anvil may be configured so that one or more of the outer surfaces of the anvil 140 may form part of the outer circumferential surface 130 of the drum 112. As such, the anvil 140 may be rotated so that more than one outer surface of the anvil 140 can be utilized before the anvil 140 needs to be replaced.

The anvil 140 may extend the entire width W of the shell segment 122. The outer surface 146a of the anvil may be located at the outer radial distance $R_O$ that is the same radial distance as the outer surface 129 of the adjacent shell members 121 such that the outer circumferential surface 130 of the drum 112 is continuous. The outer surface 146 of the anvil 140 may be curved or flat. The anvil 140 may be positioned along the outer circumferential surface 130 of the drum 112 where the elastic substrate is to be cut into discrete lengths of elastic substrate. The anvil 140 may be made of any suitable material capable of withstanding pressure and generation of heat from the cutter such as tool steel or carbide.

Figure 6:
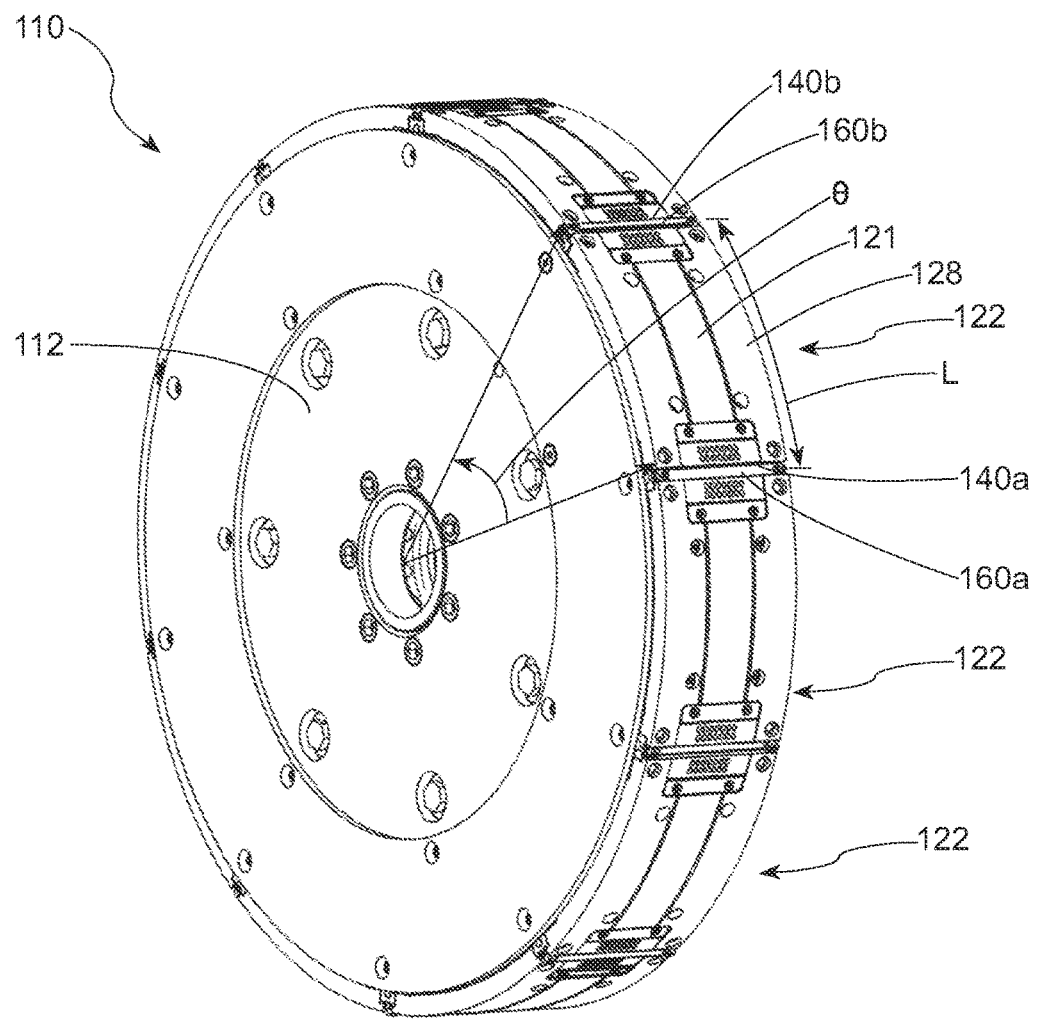
FIG. 6 is a perspective, side view of a rotary drum apparatus.
Figure 7:
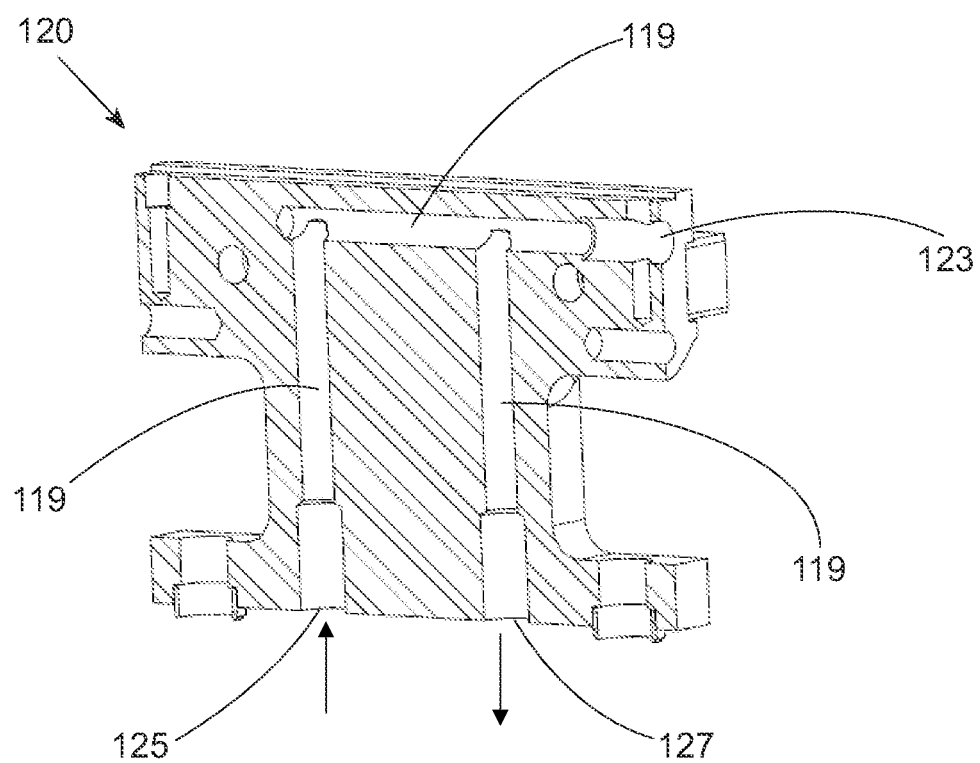
FIG. 7 is a sectional view of a support member.

As shown in FIG. 6, each shell segment 122 in a set may be defined by a contact angle θ that is subtended by an outer surface 128 of the shell segment 122 that extends from a first edge 160a of an anvil 140a to the first edge 160b of a subsequent anvil 140b. For clarity, the following paragraph assumes that each set of shell segments 122 of the rotary drum apparatus 110 combines to form the outer circumferential surface 130 at the maximum radial distance $R_M$ from the axis of rotation 114. It is to be appreciated that the contact angle θ for a shell segment may correspond with a discrete length of elastic substrate of a predetermined size. As such, each set of shell segments 122 may include shell segments 122 having a contact angle θ corresponding with a different size discrete length of elastic substrate. The total contact angle for all shell segments 122 in a set is 360 degrees, and thus, the total number of shell segments 122 in a set is dependent upon the contact angle θ of each shell segment 122 in the set. Therefore, the larger the contact angle θ of a shell segment 122 in a set, the fewer number of shell segments 122 a set will include; likewise, the smaller the contact angle θ of the shell segments in the set, the greater number of shell segments 122 a set will include. In some configurations, the contact angle θ of an individual shell segment 122 may be, for example, from 15 degrees to 60 degrees. For example, one set may include shell segments 122 having a contact angle θ of 25 degrees, corresponding with a particular size discrete length of elastic substrate, while another set of shell segments 122 may include shell segments having a contact angle θ of 45 degrees, corresponding with a different size discrete length of elastic substrate With reference to FIG. 2A, the anvils may be positioned for cutting the continuous length of substrate 170 into discrete lengths of elastic substrate 102. Over time, the anvils 140 may increase in temperature from the pressure of the cutter 184. In some exemplary configurations, the rotary drum apparatus 110 may be configured to cool the anvils 140 to prevent the anvils 140 from over-heating. As shown in FIG. 7, the support member 120 may include a cooling channel 119 for cooling an anvil connected with the support member 120 using glycol. The support member 120 may have an inlet 125 and an outlet 127. In order to locate a cooling channel 119 relatively near the anvil, the support member 120 may include a side opening 123. Glycol may be supplied to the cooling channel 119 in various ways.

Figure 8:
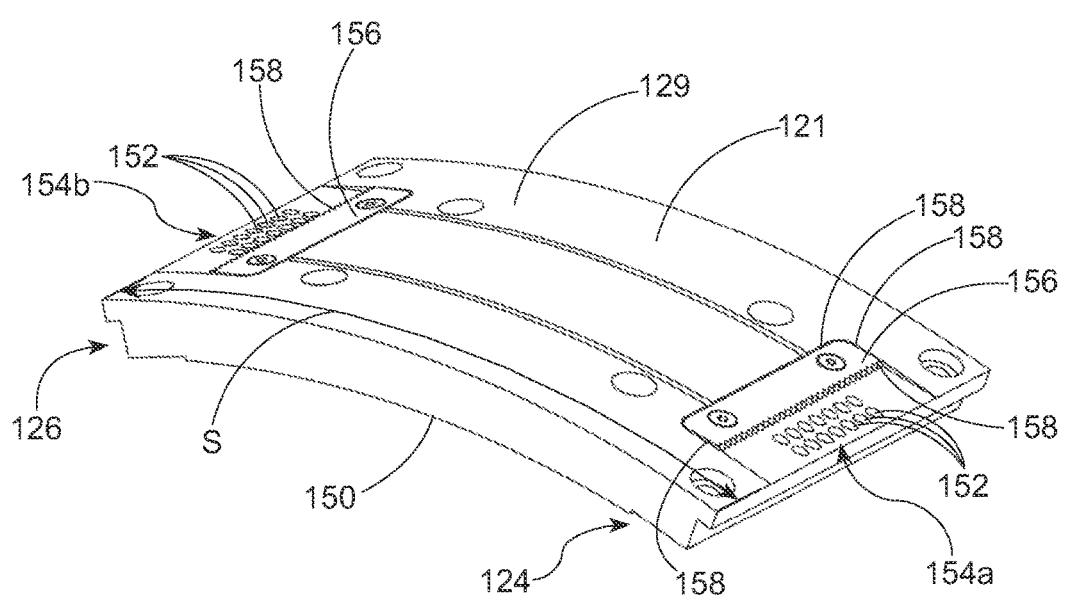
FIG. 8 is a perspective, side view of a shell member.

With reference to FIGS. 4 and 8, each shell member 121 may include vacuum apertures 152 that are in fluid communication with a vacuum member 148. The vacuum apertures 152 may be arranged into vacuum regions 154. A first vacuum region 154a may be located relatively near the first end 124 of the shell member 121 and a second vacuum region 154b may be located relatively near the second end 126 of the shell member 121. Each shell member 121 may have a vacuum region 154 of vacuum apertures 152 disposed along first and second ends 124, 126 of the shell member 121. It is to be appreciated that the vacuum apertures 152 and/or vacuum regions 154 may be arranged in various configurations and located in various positions on a shell member 121. In some exemplary configurations, a vacuum region 154 may extend from the first end 124 of a shell member 121 to the second end 126 of a shell member 121. While the vacuum apertures 152 shown in FIG. 8 are substantially circular in shape, it is to be appreciated that the vacuum apertures 152 may be of various shapes and sizes.

As shown in FIG. 4, the shell segment 122 may include a vacuum member 148 that is connectable with the inner surface 150 of a shell member 121. The same size vacuum member 148 may be connectable with one or more sets of shell segments having different circumferential lengths L. However, it is to be appreciated that each set of shell segments 122 that is configured for a different size discrete length of elastic substrate may have a different size vacuum member 148. The vacuum member 148 may be connected with the shell member 121 in various ways, such as, for example, using bolts, screws, pins, tab and slot connections, or keys and matching key ways. The vacuum member 148 may connect with the shell member 121 to form a gas-tight seal. The vacuum member 148 may be made of various materials that are capable of holding a vacuum pressure. For example, the vacuum member may be made of steel, aluminum, or plastic.

As shown in FIGS. 1, 4, and 8, the shell segments 122 may also include grip plates 156 that are connected with the outer surface 129 of the shell member 121. A grip plate 156 may be located adjacent to vacuum regions 154 at each of the first and second ends 124, 126 of the shell member 121. The grip plate 156 may be defined by one or more edges 158. One or more of the edges 158 may have a rough surface. The rough surface of the grip plate 156 may help hold the discrete length of elastic substrate on the first outer circumferential surface 130 of the drum 112 in a stretched state. It is to be appreciated that one or more grip plates 156 may be connected with each shell member 121 in various configurations. While it is shown in FIG. 8 that the grip plate 156 is substantially rectangular in shape, the grip plate 156 may be configured in various shapes and sizes. In addition, the grip plate 156 may be integral with, or separate from, the shell member 121. The grip plate may be made from stainless steel or tool steel, for example.

Figure 9:
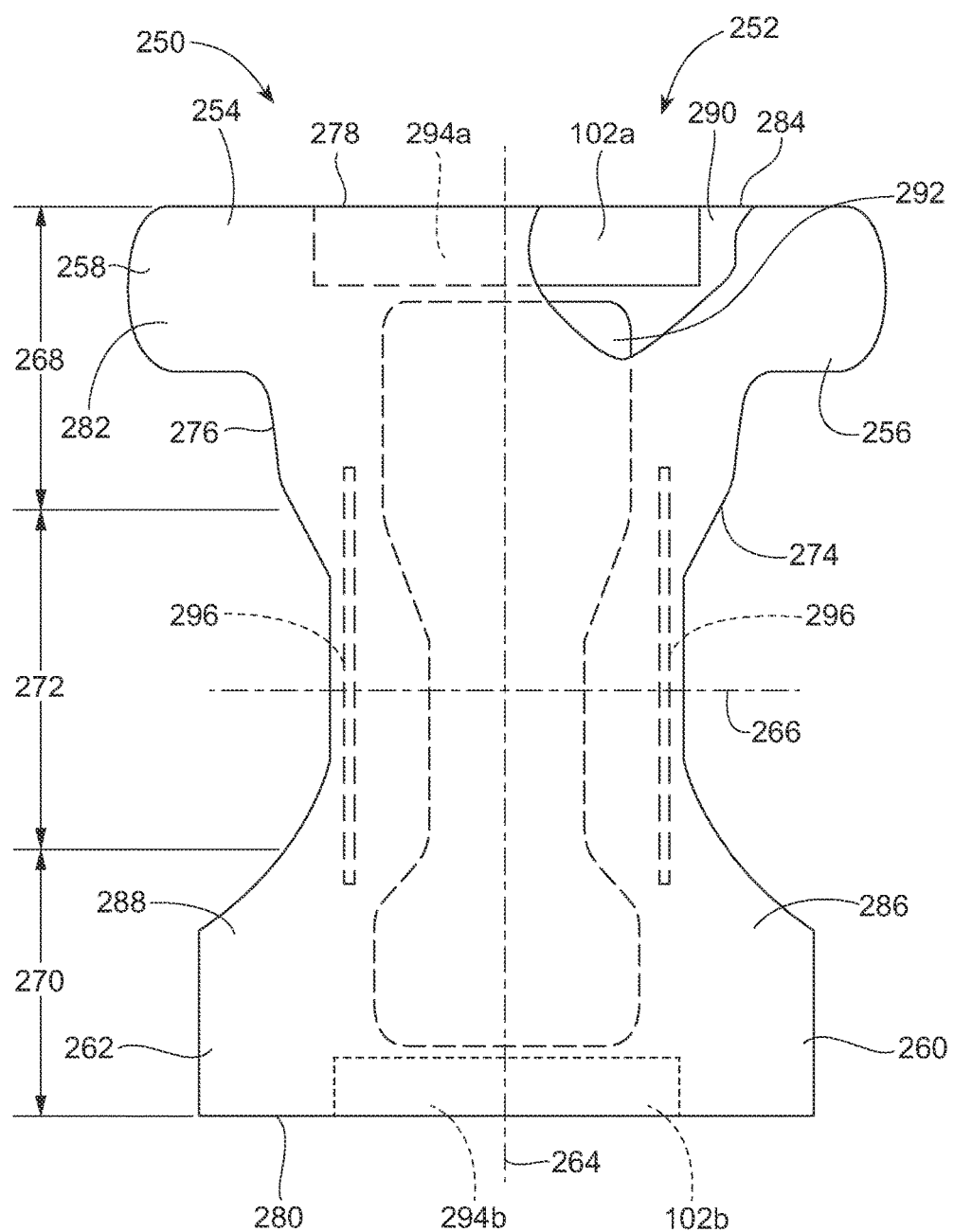
FIG. 9 is a partially cut-away, plan view of a disposable absorbent article having elastic waistbands.

A number of different products may be manufactured in accordance with the methods and apparatuses described herein. For the purposes of a specific illustration, FIG. 9 shows one example of a disposable absorbent article 250 in the form of a diaper 252 that may include discrete lengths of elastic substrate 102a and 102b formed in accordance with the present disclosure. In particular, FIG. 9 is a plan view of one embodiment of a diaper 252 including a chassis 254 shown in a flat, unfolded condition, with the portion of the diaper 252 that faces a wearer oriented towards the viewer. A portion of the chassis structure is cut-away in FIG. 9 to more clearly show the construction of and various features that may be included in exemplary configurations of the diaper.

As shown in FIG. 9, the diaper 252 includes a chassis 254 having a first ear 256, a second ear 258, a third ear 260, and a fourth ear 262. To provide a frame of reference for the present discussion, the chassis is shown with a longitudinal axis 264 and a lateral axis 266. The chassis 254 is shown as having a first waist region 268, a second waist region 270, and a crotch region 272 disposed intermediate the first and second waist regions. The periphery of the diaper is defined by a pair of longitudinally extending side edges 274, 276; a first outer edge 278 extending laterally adjacent the first waist region 268; and a second outer edge 280 extending laterally adjacent the second waist region 270. As shown in FIG. 9, the chassis 254 includes an inner, body-facing surface 282, and an outer, garment-facing surface 284. As shown in FIG. 9, the chassis 254 of the diaper 252 may include an outer covering layer 286 including a topsheet 288 and a backsheet 290. An absorbent core 292 may be disposed between a portion of the topsheet 288 and the backsheet 290. As discussed in more detail below, one or more of the regions may be stretchable and may include an elastomeric material or layered elastic substrate as described herein. As such, the diaper 252 may be configured to adapt to a specific wearer's anatomy upon application and to maintain coordination with the wearer's anatomy during wear.

Although the first and second ears 256, 258 as well as the third and fourth ears 260, 262 shown in FIG. 9 are illustrated as being integrally formed with the chassis 254, it is to be appreciated that other embodiments may include ears that are discrete elements connected with the chassis. In some embodiments, the ears are configured to be stretchable. The ears may also include one or more fastener elements adapted to releasably connect with each other and/or other fastener elements on the chassis. A more detailed discussion of stretchable ears can be found in U.S. Pat. Nos. 4,857,067; 5,151,092; 5,674,216; 6,677,258; 4,381,781; 5,580,411; and 6,004,306.

As shown in FIG. 9, the diaper 252 may include leg cuffs 296 that may provide improved containment of liquids and other body exudates. The leg cuffs 296 may be disposed in various ways on the diaper 252. For example, the leg cuffs 296 may be disposed on the outer, garment-facing surface 284 of the chassis 254; the inner, body-facing surface 282; or between the inner and outer facing surfaces 282 or 284. Leg cuffs 296 may also be referred to as leg bands, side flaps, barrier cuffs, or elastic cuffs. U.S. Pat. No. 3,860,003 describes a disposable diaper that provides a contractible leg opening having a side flap and one or more elastic members to provide an elasticized leg cuff (a gasketing cuff). U.S. Pat. Nos. 4,808,178 and 4,909,803 describe disposable diapers having "stand-up" elasticized flaps (barrier cuffs). U.S. Pat. Nos. 4,695,278 and 4,795,454 describe disposable diapers having dual cuffs, including gasketing cuffs and barrier cuffs.

The diaper may be provided in the form of a pant-type diaper or may alternatively be provided with a re-closable fastening system, which may include fastener elements in various locations to help secure the diaper in position on the wearer. For example, fastener elements may be located on the first and second ears and may be adapted to releasably connect with one or more corresponding fastening elements located in the second waist region. It is to be appreciated that various types of fastening elements may be used with the diaper. In one example, the fastening elements include hook & loop fasteners, such as those available from 3M or Velcro Industries. In other examples, the fastening elements include adhesives and/or tap tabs, while others are configured as a macrofastener or hook (e.g., a MACRO or "button-like" fastener). Some exemplary fastening elements and systems are disclosed in U.S. Pat. Nos. 3,848,594; 4,662,875; 4,846, 815; 4,894,060; 4,946,527; 5,151,092; and 5,221,274. Additional examples of fasteners and/or fastening elements are discussed in U.S. Pat. Nos. 6,251,097 and 6,432,098; and U.S. Patent Publication Nos. 2007/0078427 and 2007/0093769. Other fastening systems are described in more detail in U.S. Pat. Nos. 5,595,567; 5,624,427; 5,735,840; and 5,928,212. The fastening system may also provide a means for holding the article in a disposal configuration as disclosed in U.S. Pat. No. 4,963,140.

The absorbent article may also include discrete lengths of elastic substrate 102a and 102b such as shown in FIG. 9 in the form of first and second waistbands 294a and 294b. The first and second waistbands 294a and 294b may provide improved fit and waste containment. The first and second waistbands 294a and 294b may be located in the first waist region 268 and/or the second waist region 270. The first and second waistbands 294a and 294b may be configured to elastically expand and contract to dynamically fit the wearer's waist.

The first and second waistbands 294a and 294b can be incorporated into the diaper in accordance with the methods discussed herein and may extend at least longitudinally outwardly from the absorbent core 292 and generally form at least a portion of the first and/or second outer edges 278, 280 of the diaper 252. In addition, the first and second waistbands 294a and 294b may extend laterally to include the ears. In addition, the first and second waistbands 294a and 294b may be disposed on the outer, garment-facing surface 284 of the chassis 254; the inner, body-facing surface 282; or between the inner and outer facing surfaces. It is to be appreciated that the first waistband 294a and the second waistband 294b shown in FIG. 9 may comprise the same materials and/or may have the same structure. While in other exemplary configurations, the first waistband 294a and the second waistband 294b may comprise different materials and/or may have different structures. The first and second waistbands 294a and 294b may be constructed in a number of different configurations including those described in U.S. Patent Application No. 61/499,294; and U.S. Patent Publication Nos. 2007/0142806; 2007/0142798; and 2007/0287983.

The discrete lengths of elastic substrate may comprise various materials and/or layers of materials. For example, the substrate may include an elastic material interposed between layers of nonwovens webs. Nonwoven webs include, for example, natural materials (e.g., wood or cotton fibers), synthetic fibers (e.g., polyolefins, polyamides, polyester, polyethylene, or polypropylene fibers) or a combination of natural and/or synthetic fibers. The elastic material may comprise elastic strands, ribbons, films, or combinations thereof. In some examples, the substrate may be constructed from a single elastic or poly film (e.g., polyethylene or polypropylene). In yet other examples, the substrate may be constructed from a single layer nonwoven or activated nonwoven.

Exemplary nonwoven webs include spunbond-meltblown-meltblown-spunbond (SMMS) nonwovens having a basis weight of 10 grams per square meter (gsm) and spunbond-meltblown-spunbond (SMS) nonwovens having a basis weight of 10 gsm, both of which are manufactured by Avgol Ltd. of Tel Aviv, Israel. Other exemplary nonwoven webs include spunbond-meltblown-meltblown-meltblown-spunbond (SMMMS) nonwovens having a basis weight of 11 gsm, which is manufactured by Fibertex Nonwovens A/S of Aalborg, Denmark. Exemplary elastic strands have a mass-density of 680 decitex and are manufactured by Hyousong of Seoul, Korea. Other exemplary elastic strands have a decitex of 680 and are manufactured by Invista of Wichita, Kans. under the designation Lycra®.

Components of the disposable absorbent article (i.e., diaper, disposable pant, adult incontinence article, sanitary napkin, pantiliner, etc.) described in this specification can at least partially be comprised of bio-sourced content as described in US 2007/0219521A1 Hird, et al published on Sep. 20, 2007, US 2011/0139658A1 Hird, et al published on Jun. 16, 2011, US 2011/0139657A1 Hird, et al published on Jun. 16, 2011, US 2011/0152812A1 Hird, et al published on Jun. 23, 2011, US 2011/0139662A1 Hird, et al published on Jun. 16, 2011, and US 2011/0139659A1 Hird, et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing zone nonwovens and film bases.

In at least one exemplary configuration, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B.

In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (e.g., Wiley® mill), and a representative sample of suitable mass taken from the randomly mixed particles.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A rotary drum apparatus comprising:
   a drum rotatable about an axis of rotation, wherein the drum comprises an inner circumferential surface comprising a plurality of connection sites spaced circumferentially around the inner circumferential surface of the drum;
   a set of first shell segments having a first number of the first shell segments releasably connectable with the plurality of connection, and each of the first shell segments having a first outer surface, and wherein the first outer surfaces combine to form a first outer circumferential surface surrounding the axis of rotation and defining a maximum radial distance from the axis of rotation;
   a set of second shell segments having a second number of the second shell segments releasably connectable with the plurality of connection sites, and each of the second shell segments having a second outer surface, and wherein the second outer surfaces combine to form a second outer circumferential surface surrounding the axis of rotation and defining a second radial distance;
   wherein the rotary drum apparatus is configurable between a first orientation and a second orientation, wherein in the first orientation the set of first shell segments are connected to the plurality of connection sites, and wherein in the second orientation the set of second shell segments are connected to the plurality of connection sites;
   wherein the first number of the first shell segments is different than the second number of the second shell segments;
   wherein the maximum radial distance is greater than the second radial distance;

wherein each of the first and second shell segments comprise a shell member releasably connectable with the support member, the shell member having a curved outer surface; and the rotary drum apparatus further comprises a vacuum member releasably connectable with each of the shell members, wherein each of the shell members further comprise a plurality of vacuum apertures in fluid communication with the vacuum member.

2. The rotary drum apparatus of claim 1, wherein the inner circumferential surface is located at an inner radial distance, wherein the inner radial distance is less than the maximum radial distance.

3. The rotary drum apparatus of claim 1, wherein at least one of the first outer surface and the second outer surface is curved.

4. The rotary drum apparatus of claim 1, wherein each of the first and second shell segments comprise:

a support member releasably connectable with the drum.

5. The rotary drum apparatus of claim 4, wherein each of the first and second shell segments comprise an anvil releasably connectable with the support member, the anvil comprising a first outer surface that forms a part of the outer circumferential surface of the rotary drum apparatus.

6. The rotary drum apparatus of claim 5, wherein the first outer surface of the anvil is flat.

7. The rotary drum apparatus of claim 5, wherein the anvil further comprises a second outer surface, wherein the second outer surface of the anvil is capable of forming a part of the outer circumferential surface of the rotary drum apparatus.

8. The rotary drum apparatus of claim 4, comprising a grip plate connectable with the curved outer surface of the shell member.

9. The rotary drum apparatus of claim 4, wherein each support member comprises a cooling channel.

10. The rotary drum apparatus of claim 4, wherein the support members are releasably connectable with each of the plurality of connection sites.

11. The rotary drum apparatus of claim 4, wherein:

the vacuum member of the first shell segments each comprise a first vacuum member of a first size; and the vacuum member of the second shell segments each comprise a second vacuum member of a second size, wherein the first size is different from the second size.

12. The rotary drum apparatus of claim 1, wherein the first outer surfaces of the first shell segments define equal circumferential lengths, and the second outer surfaces of the second shell segments define equal circumferential lengths.

13. The rotary drum apparatus of claim 1, wherein the circumferential length of the first shell segments are greater than the circumferential length of the second shell segments.

14. The rotary drum apparatus of claim 1, wherein when the second shell segments are connected with the inner circumferential surface of drum, the second outer surfaces combine to form the second outer circumferential surface located at the maximum radial distance from the axis of rotation.

* * * * *